(12) United States Patent
Lorimer et al.

(10) Patent No.: US 10,617,859 B2
(45) Date of Patent: Apr. 14, 2020

(54) VALVE FOR MEDICAL IMPLANT DELIVERY SYSTEM

(71) Applicant: Lombard Medical Limited, Didcot, Oxfordshire (GB)

(72) Inventors: Kevin Lorimer, Didcot (GB); Duncan Keeble, Didcot (GB)

(73) Assignee: Lombard Medical Limited (GB)

( * ) Notice: Subject to any disclaimer, the term of this patent is extended or adjusted under 35 U.S.C. 154(b) by 0 days.

(21) Appl. No.: 15/116,869

(22) PCT Filed: Feb. 6, 2015

(86) PCT No.: PCT/GB2015/050335
§ 371 (c)(1),
(2) Date: Aug. 5, 2016

(87) PCT Pub. No.: WO2015/118345
PCT Pub. Date: Aug. 13, 2015

(65) Prior Publication Data
US 2017/0165466 A1 Jun. 15, 2017

(30) Foreign Application Priority Data
Feb. 7, 2014 (GB) .................................. 1402149.7

(51) Int. Cl.
*A61M 39/06* (2006.01)

(52) U.S. Cl.
CPC ........ *A61M 39/06* (2013.01); *A61M 39/0613* (2013.01); *A61M 39/0693* (2013.01); *A61M 2039/062* (2013.01); *A61M 2039/0673* (2013.01)

(58) Field of Classification Search
CPC .............. A61M 39/06; A61M 39/0613; A61M 39/0693; A61M 2039/062; A61M 2039/0626; A61M 2039/0633
See application file for complete search history.

(56) References Cited

U.S. PATENT DOCUMENTS

| | | | |
|---|---|---|---|
| 5,158,553 A | 10/1992 | Berry et al. | |
| 5,197,955 A * | 3/1993 | Stephens | A61B 17/3462 604/167.01 |
| 5,211,370 A | 5/1993 | Powers et al. | |
| 7,172,580 B2 | 2/2007 | Hrushka et al. | |
| 8,235,946 B2 | 8/2012 | Molgaard-Nielsen | |
| 2004/0178586 A1 * | 9/2004 | Junge | A61M 39/0613 277/602 |

(Continued)

FOREIGN PATENT DOCUMENTS

| | | |
|---|---|---|
| EP | 0 538 060 A1 | 4/1993 |
| WO | WO 2005/058409 A1 | 6/2005 |
| WO | WO 2009/058309 A1 | 5/2009 |

OTHER PUBLICATIONS

International Search Report, PCT/GB2015/050335, dated May 21, 2015.

*Primary Examiner* — Katrina M Stransky
(74) *Attorney, Agent, or Firm* — Craig A. Fieschko, Esq.; DeWitt LLP

(57) ABSTRACT

A valve (100) for use in delivering a medical device comprises first and second ends and an hourglass shaped centre section defining an aperture (34) for accepting a guidewire. The application of torsion about the centre section closes the aperture to seal against the guidewire.

20 Claims, 1 Drawing Sheet

(56) References Cited

U.S. PATENT DOCUMENTS

2009/0125103 A1\* 5/2009 Molgaard-Nielsen ........................ A61M 39/0613
                                                                    623/2.12
2011/0054405 A1   3/2011 Whiting et al.

\* cited by examiner

VALVE FOR MEDICAL IMPLANT DELIVERY SYSTEM

FIELD OF THE INVENTION

The present invention relates to a valve for use in a delivery system for a medical implant, and in particular a delivery system for an implantable stent graft.

BACKGROUND OF THE INVENTION

An endovascular stent graft is designed to exclude the flow of blood to an aneurysm that has been formed within the wall of the lumen (for example, the aorta). This is achieved by accessing the aneurysm via an artery, usually within the patient's leg, with a system designed to deliver, position and deploy the stent graft so that it bridges and seals off the aneurysm.

In order to deliver a stent graft to the locus of the aneurysm, it is usually collapsed (that is, reduced in diameter), loaded in a delivery system (where it is retained in the collapsed configuration by a catheter sheath) and delivered to the aneurysm where it is positioned and deployed by expanding its diameter to seal off the aneurysm as described above.

The stent graft delivery system, which contains the stent graft, is inserted into the patient over a guide wire that has already been placed into the patients' arterial system. This type of 'over-the-wire' technique is very well known in endovascular surgery (performing vascular surgery from within the vessel) and permits a variety of catheter-based instruments and devices to be placed into the patient's arteries by passing them over the same guide wire. Examples of such instruments and devices include diagnostic catheters, angioplasty and molding balloons, snares, stents, occluders and endovascular stent grafts.

Once the stent graft is in position over the guidewire, deployment of the stent graft is carried out by the surgeon operating a series of control wires (for example) to manipulate the stent graft remotely in order to move it into the correct position (both longitudinally and rotationally) and to control its shape. The stent graft may then be deployed by partially withdrawing the catheter sheath to enable the stent graft to expand in diameter at the locus of the aneurysm. The control wires pass from a control mechanism operated by the surgeon through the delivery catheter and are connected to the stent graft. It is necessary to employ a valve in the sheath which allows a plurality of control wires and a variety of combinations of guidewires, stent grafts and other delivery system components to pass therethrough but which prevents the patient's blood from leaking out of the delivery sheath.

Preferably the delivery system is designed in such a way that the control wires and other mechanisms can be removed completely from the patient through the sheath and valve, leaving the sheath and valve behind in the patient's artery. This will provide an access conduit for other instruments or devices to be passed through the valve and sheath and into the patient's arteries, without losing blood through the sheath and without the need to replace the sheath with another catheter or sheath. In this way, the valve described herein has a first application as an essential component of a stent graft delivery system and a second application as a component of a valved vascular access sheath. Those skilled in the art will be able to identify other applications of the valve.

Various valves are disclosed in EP 0550069 A1 (Guy); US 2011/251565 A1 (Malewicz); WO 98/17341 A2 (Mayo Foundation); WO 03/048616 A1 (Cook, Inc); and US 2010/036504 A1 (Sobrino-Serrano et al.).

US 2010/0224802 A1 (Mialhe) discloses a valve for medical instruments which includes a cylindrical passage which can be at least partially sealed by twisting the valve in order to deform torsionally a flexible section of the passage wall. The disadvantage of this system is that it requires positive intervention from the surgeon in order to seal the valve, in addition to all of the other tasks which the surgeon needs to undertake.

U.S. Pat. No. 7,753,952 B2 (Mialhe) discloses a similar valve with similar short comings. Other valves of this type are disclosed in U.S. Pat. Nos. 7,445,623, 8,118,275 and 6,808,520 (all in the name of the same applicant).

FR 2,863,504 (Mialhe) discloses a similar valve to those discussed above which can be fixed in the closed position (under torsion) but which is releasable with user intervention. In particular, radial grooves secure the movable part in the angular position.

The principal disadvantage with these prior art valves is that they require surgeon intervention in order to operate the valve. There are additional problems however such as achieving a good seal when the guidewire is approximately the same diameter as the internal diameter of the valve hole (when the valve is in the "sealed" position). Prior art valves also have difficulty dealing with a wide range of diameters of guidewires or other instruments and devices when they are introduced through the valve and into the sheath.

The majority of prior art valves use a silicone seal which flexes in order that the valve hole can be dilated when guidewires are inserted into the valve. The expansion range of the silicone seal is an important property in determining the sealing characteristics of the valve. In general, silicone has an expansion range of 500-1000%, which means that a 1 mm hole can expand to a diameter in the range of 5-10 mm. In order to operate effectively in a stent graft delivery system, a valve is required to provide a seal around guidewire(s) ranging from 0.9 mm to 6 mm in external diameter. This requires a valve having a hole with an internal diameter of 0.5 mm (to provide an effective seal around a 0.9 mm guidewire) and an expansion up to 6 mm. However, this requires an expansion ratio of 1200%, which is not possible with prior art silicone valves.

SUMMARY OF THE INVENTION

The inventive realisation of the applicant is that the above technical problems can be at least partially addressed by providing a valve which preferably has an "hour-glass" configuration which can be placed under torsion to close down the valve hole. This can be provided in pre-twisted form and/or with O-rings mounted thereon in order to provide additional compression.

In accordance with a first aspect of the present invention, there is provided a valve for use in delivering a medical device (preferably using endovascular techniques), comprising: a body having a first end and a second end disposed along a longitudinal axis, a wall defining a passage between the first and second ends, means disposed between the first and second ends defining an aperture, the aperture having a first diameter when in an unstressed state, wherein said first diameter is less than the internal diameter of the passage at least one of the first and second ends, said means being formed of a flexible material, whereby when an element having an external diameter greater than the first diameter is inserted into the aperture, the diameter of the aperture increases to accommodate the element and to create a seal around the element, and whereby when torsion is applied to said means, the diameter of the aperture reduces.

It has been found that the provision of an aperture having an unstressed diameter which is less than the internal diameter of the passage at one or both of its ends (that is, preferably an hour-glass shaped passage) enables the provision of a valve which can seal a much wider range of diameters than prior art valves.

Preferably, the aperture a first diameter of up to 1 mm and most preferably from 0.5 mm to 0.9 mm.

The means defining the aperture is preferably formed by the internal surface of the wall defining the passage between the first and second ends of the valve and is preferably formed from the same type of material as the wall (for example, silicone).

The first end of the valve may be rotatable relative to the second end about the longitudinal axis of the valve so as to apply torsion to said means defining an aperture. In a preferred embodiment, the valve additionally comprises means for locking the rotational position of the first end relative to the second end, whereby the means defining an aperture is retained under torsion.

The advantage of providing said means for locking the valve is that the valve can be provided in "pre-twisted" form, with the degree of torsion being fixed to cover the range of scenarios for which it is intended that the valve is to be used. For example, a valve can be provided with a pre-twist in the range from 180° to 900°, and most preferably about 250° to 600°. In a preferred embodiment, a pre-twist of 360° is used. The provision of a pre-twisted valve means that the surgeon does not need to twist the valve himself in order to operate it, thereby leaving his hands free to operate the guidewires necessary to deploy the stent graft.

In one embodiment, the valve may additionally comprise means for resisting increase of the diameter of the valve aperture, such as an annular element (or O-ring) disposed around said means defining an aperture, whereby the annular element is formed of a resilient material. For example, an O-ring having an internal diameter equal to or slightly greater than the external diameter of the valve at the narrowest point of the hour-glass acts effectively to increase the sealing capability of the valve, due to the resilient nature of the O-ring. Thus, an O-ring having a particular internal diameter and/or resistance to expansion can be selected according to the surgeon's requirements.

In a preferred embodiment, the wall defining a passage between the first and second ends of the valve is in a state of longitudinal tension between the first and second ends (referred to as longitudinal stress). For example, a passage which is 10 mm long in its unstressed state can be stretched to 18 mm in length. In general, a longitudinal stress from 120% to 150% is preferred. It has been found that a valve which is under longitudinal stress has better sealing characteristics than one that is not.

The valve should have adequate 'shelf-life' while in the dilated state. The design of the valve provides additional extensibility that allows the material to be used in a state where zero, or very minimal, creep occurs.

Preferably, the valve is manufactured from a material having high extensibility and very low creep, such as silicone rubber, but other materials with similar properties can be employed.

Beneficially, the valve includes a tubular liner, formed for example from ePTFE which has been found to improve the performance of several characteristics of the valve. In particular, it has been found to reduce the force required to pass items through the valve, it has been found to remove the need for liquid lubricants, it has been found to preserve the life of the valve by preventing adhesion or 'stricktion' of adjacent faces of the valve lumen and it guides items passed through the valve to follow the centre-line, minimizing the risk of impingement which could lead to disruption of the alignment of the valve component.

In an alternative embodiment to those described above, the valve may comprise a plurality of means defining an aperture which are disposed sequentially between the first and second ends of the valve. This gives a particularly effective seal for high pressure situations.

BRIEF DESCRIPTION OF THE DRAWINGS

A number of preferred embodiments of the present invention will now be described by way of example, with reference to the drawings, in which.

DETAILED DESCRIPTION OF EXEMPLARY VERSIONS OF THE INVENTION

Figure 1:
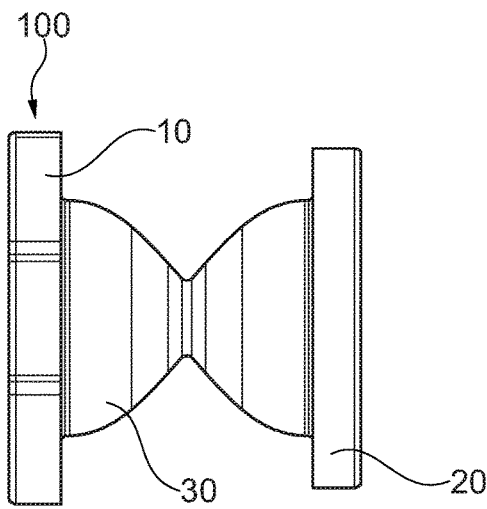
FIG. 1 shows a plan view of a valve in accordance with the invention.
Figure 2:
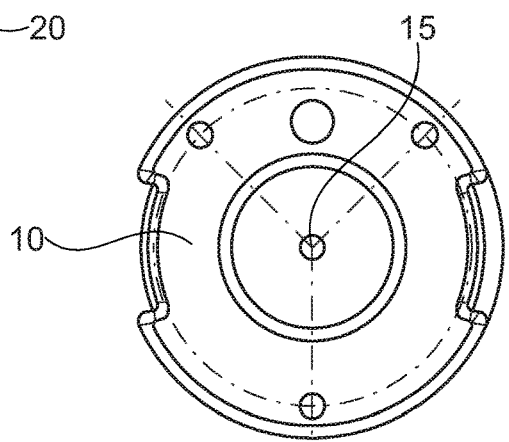
FIG. 2 is an end view from one end of the valve shown in FIG. 1.
Figure 3:
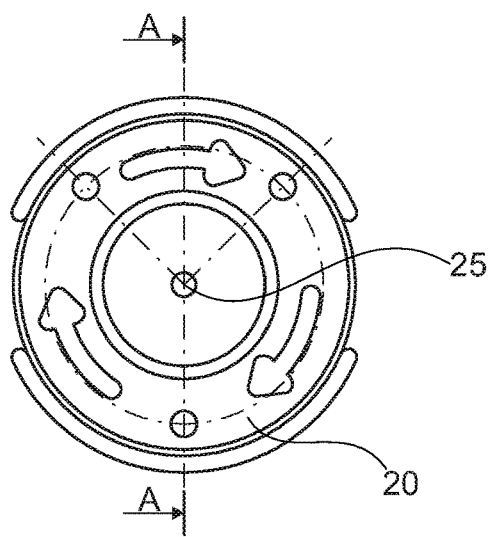
FIG. 3 is an end view of the other end of the valve shown in FIG. 1.

Turning to the drawings, FIG. 1 shows a valve 100 with proximal end 10 and distal end 20 both formed of circular section of plastics material. Proximal and distal ends 10, 20 have proximal aperture 15 and distal aperture 25 respectively at their centres.

Figure 4:
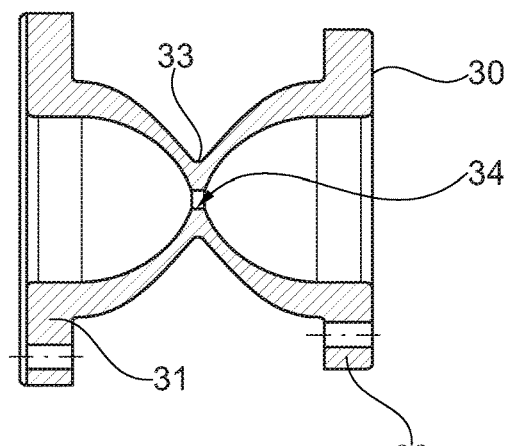
FIG. 4 is a cross-sectional view of the valve of FIG. 1.

"Hour-glass" valve wall 30 is formed of silicone and disposed between proximal and distal ends 10/20. The shape of valve wall 30 can be seen in more detail in FIG. 4. Valve wall 30 has proximal flange 31 which fits into proximal end 10 and has distal flange 32 which fits into distal end 20. The valve wall 30 has an hour-glass shape with a waisted section 33 having aperture 34 therein for accepting guidewires in use.

The dimensions for each of the component parts (which are preferred dimensions only) are shown on FIGS. 1-4.

In use, a guidewire (not shown) is inserted through proximal aperture 15, through valve aperture 35 and exits out of distal aperture 25. Valve 100 can then be closed to seal around the guidewire by rotating distal end 20 relative to proximal end 10 in order to apply torsion to valve wall 30 and to close down the internal diameter of aperture 34. The valve can be locked in to the twisted position or in an alternative embodiment the valve can be provided pre-twisted depending on the use to which it is to be put.

In order to release the guidewire it can either simply be pulled out of the valve 100 or alternatively the valve can be untwisted first in order to allow the guidewire to be removed more easily.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in UK patent application number 1402149.7, from which this application claims priority, and in the abstract accompanying this application are incorporated herein by reference.

The invention claimed is:

1. A valve for use in delivering a medical device, the valve including:
 a body having a first end and a second end disposed along a longitudinal axis, and a wall defining a passage between the first and second ends,
 a flexible member disposed about the passage, the flexible member being spaced from each of the first and second ends and defining an aperture along the passage, the aperture having a first diameter when in an unstressed state, wherein:
 (1) the first diameter is less than the internal diameter of the passage at one or both of the first and second ends, and
 (2) when an element having an external diameter greater than the first diameter is inserted into the aperture, the diameter of the aperture increases to accommodate the element and to create a seal around the element,
 wherein the valve is fixed in a twisted state:
 a. with the flexible member under a fixed degree of torsion,
 b. with the first end of the body being nonrotatably secured relative to the second end,
 c. with the wall defining the passage being in longitudinal tension between the first and second ends of the body, and
 without any element being within the aperture of the flexible member.

2. The valve of claim 1 wherein the aperture has a first diameter of up to 1 mm.

3. The valve of claim 1 wherein the first diameter is less than the internal diameter of the passage at both the first and the second ends.

4. The valve of claim 1 wherein the wall is configured so that the passage is hour-glass shaped.

5. The valve of claim 1 wherein the flexible member is integrally formed as a single piece with the body.

6. The valve of claim 1 wherein the flexible member is formed of the same material as the wall.

7. The valve of claim 1 wherein the first end is rotatable relative to the second end about the longitudinal axis so as to apply torsion to the flexible member.

8. The valve of claim 1 wherein the first end is locked into a position in which it has been rotated 360° relative to the second end.

9. The valve of claim 1 wherein the flexible member is in a permanent state of torsion, such that the aperture has a diameter which is less than the first diameter.

10. The valve of claim 1 further including resistance means for resisting increase of the diameter of the aperture.

11. The valve of claim 10 wherein the resistance means comprises an annular element formed of a resilient material, the annular element being disposed around the flexible member.

12. The valve of claim 1 wherein the body is stretched along its longitudinal axis to a length which is from 120%-150% of its length when not under longitudinal tension.

13. The valve of claim 1 having several flexible members disposed sequentially between the first and second ends.

14. The valve of claim 1 further including a tubular liner.

15. A valve for use in delivering a medical device, the valve including:
 a body having a wall defining a passage extending between a first end and a second end, the passage converging inwardly from the first end and from the second end to define a narrowed aperture between the first and second ends,
 wherein the wall is flexible about the aperture, whereby the aperture seals about an element of a medical device inserted therein if the element has a diameter greater than the diameter of the aperture,
 wherein the valve is fixed in a twisted state, with one of the first and second ends of the body being twisted and nonrotatably fixed with respect to the other such that:
 a. the body is in a fixed degree of torsion, and
 b. the wall defining the passage is in longitudinal tension between the first and second ends of the body,
 without any element being in the aperture, whereby the diameter of the aperture is reduced prior to subsequent insertion of any element therein.

16. The valve of claim 15 wherein the body is formed of elastomeric material.

17. The valve of claim 15 wherein the internal diameter of the aperture, when the valve is not in a twisted state and the wall defining the passage is not in longitudinal tension between the first and second ends of the body, is less than the internal diameter of the passage at one or both of the first and second ends.

18. The valve of claim 15 wherein the internal diameter of the aperture, when the valve is not in a twisted state and the wall defining the passage is not in longitudinal tension between the first and second ends of the body, is less than the internal diameter of the passage at both of the first and second ends.

19. A method of delivering a medical device using the valve of claim 15, the method including the step of inserting a medical device within the reduced-diameter aperture.

20. The method of claim 19 further including the step, prior to any element being in the aperture, of tensioning the body between the first and second ends until the length of the body between the first and second ends is at least 120% of the length of the body when untensioned.

* * * * *